(12) United States Patent
Pinchuk et al.

(10) Patent No.: US 6,273,895 B1
(45) Date of Patent: Aug. 14, 2001

(54) METHOD OF MEASURING A BODY CAVITY

(75) Inventors: Leonard Pinchuk; David C. MacGregor, both of Miami, FL (US)

(73) Assignee: Corvita Corporation, Miami, FL (US)

( * ) Notice: Subject to any disclaimer, the term of this patent is extended or adjusted under 35 U.S.C. 154(b) by 0 days.

(21) Appl. No.: 09/573,294

(22) Filed: May 18, 2000

Related U.S. Application Data

(62) Division of application No. 08/466,934, filed on Jun. 6, 1995, now abandoned.

(51) Int. Cl.[7] ................................................. A61F 11/00
(52) U.S. Cl. .......................................... 606/108; 623/1.11
(53) Field of Search .................................... 606/108, 192, 606/194, 198; 623/1.11, 1.12, 1.22, 1.23

(56) References Cited

U.S. PATENT DOCUMENTS

| | | |
|---|---|---|
| 4,500,313 | 2/1985 | Young . |
| 4,787,899 | 11/1988 | Lazarus ..................................... 623/1 |
| 4,790,810 | 12/1988 | Pugh, Jr. et al. . |
| 4,921,484 | 5/1990 | Hillstead ............................... 604/104 |
| 4,954,126 | 9/1990 | Wallsten ................................. 600/36 |

(List continued on next page.)

FOREIGN PATENT DOCUMENTS

| | | |
|---|---|---|
| 0274846 | 12/1987 | (EP) . |
| 0587197 A1 | 10/1991 | (EP) . |
| 2688688 | 7/1992 | (FR) . |
| WO91/12779 | 9/1991 | (WO) . |
| WO92/19161 | 11/1992 | (WO) . |
| WO94/24961 | 11/1994 | (WO) . |
| WO96/39077 | 12/1996 | (WO) . |

OTHER PUBLICATIONS

"A Study of the Geometrical and Mechanical Properties of a Self–Expanding Metallic Stent." by Jedwab et al., Jour. of Applied Biomaterial 1993, vol. 4, pp. 77–85.

"Oesophageal Strictures", C.C. Didcott, F.R.C.S. vol. 53 Annals of the Royal College of Surgeons of England, pp. 112–126 (Aug. 1973).

*Primary Examiner*—Henry J. Recla
*Assistant Examiner*—Kevin Troung
(74) *Attorney, Agent, or Firm*—Ratner & Prestia

(57) ABSTRACT

An apparatus and method are disclosed for measuring the desired length of a prosthetic device which is to be implanted in a body cavity of a patient. The apparatus generally includes a helically coiled stent formed of a resiliently-deformable material, a plunger which is connected to the proximal end of the stent, a sheath which slides over the plunger and stent when the plunger and sheath are used to insert and removably deploy the stent into the body cavity, and a scale for measuring an indication of the length of the stent once removably deployed in the body cavity. Proximal movement of the sheath to partially deploy the stent causes a length to be indicated on the scale. According to the method of the invention, the helically coiled stent of the apparatus is placed and partially deployed within the body cavity by use of the plunger and sheath of the apparatus. Once the stent bridges the body cavity, the scale of the apparatus is used to determine the length of the deployed stent. The apparatus is then removed from the body cavity, and a stent similar to the stent of the apparatus is cut to the length indicated on the scale. In a second embodiment of the apparatus and method, the stent of the measuring apparatus is substantially non-porous to allow occlusion of side vessels extending from the body cavity. The patient is then monitored for any ill effects resulting from the occlusion.

13 Claims, 7 Drawing Sheets

U.S. PATENT DOCUMENTS

| | | | |
|---|---|---|---|
| 4,973,301 | 11/1990 | Nissenkorn . | |
| 4,998,539 | 3/1991 | Deisanti | 128/898 |
| 5,013,318 | 5/1991 | Spranza, III . | |
| 5,019,090 | 5/1991 | Pinchuk | 606/108 |
| 5,026,377 | 6/1991 | Burton et al. | 606/108 |
| 5,030,227 | 7/1991 | Rosenbluth et al. . | |
| 5,061,275 | 10/1991 | Wallsten et al. | 623/1 |
| 5,064,435 | 11/1991 | Porter | 623/12 |
| 5,071,407 | 12/1991 | Termin et al. | 604/104 |
| 5,078,720 | 1/1992 | Burton et al. | 606/108 |
| 5,152,792 | 10/1992 | Watkins et al. | 623/16 |
| 5,160,341 | 11/1992 | Brenneman et al. | 606/198 |
| 5,197,978 | 3/1993 | Hess | 623/1 |
| 5,201,757 | 4/1993 | Getb et al. | 606/198 |
| 5,224,953 | 7/1993 | Morgentaler . | |
| 5,279,561 | 1/1994 | Roucher et al. | 604/96 |
| 5,290,295 | 3/1994 | Querals et al. | 606/108 |
| 5,312,415 | 5/1994 | Palermo | 606/108 |
| 5,330,500 | 7/1994 | Song | 606/198 |
| 5,383,892 | 1/1995 | Cardon et al. | 606/198 |
| 5,391,172 | 2/1995 | Williams et al. | 606/108 |
| 5,397,355 | 3/1995 | Marin et al. | 623/12 |
| 5,411,507 | 5/1995 | Heckele | 606/198 |
| 5,415,664 | 5/1995 | Pinchuk | 606/108 |
| 5,464,408 | 11/1995 | Duc | 606/198 |
| 5,479,938 | 1/1996 | Weier . | |
| 5,607,466 | 3/1997 | Imbert et al. | 623/1 |
| 5,645,559 | 7/1997 | Hachtman et al. | 606/198 |

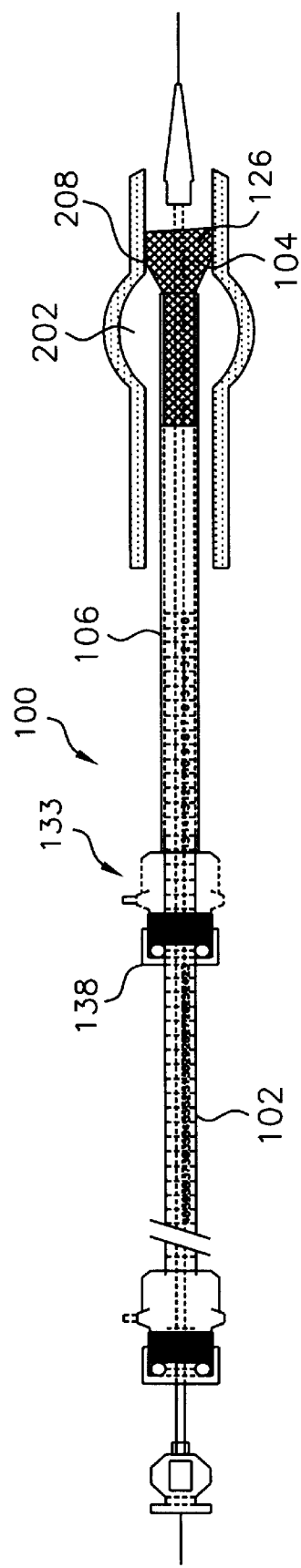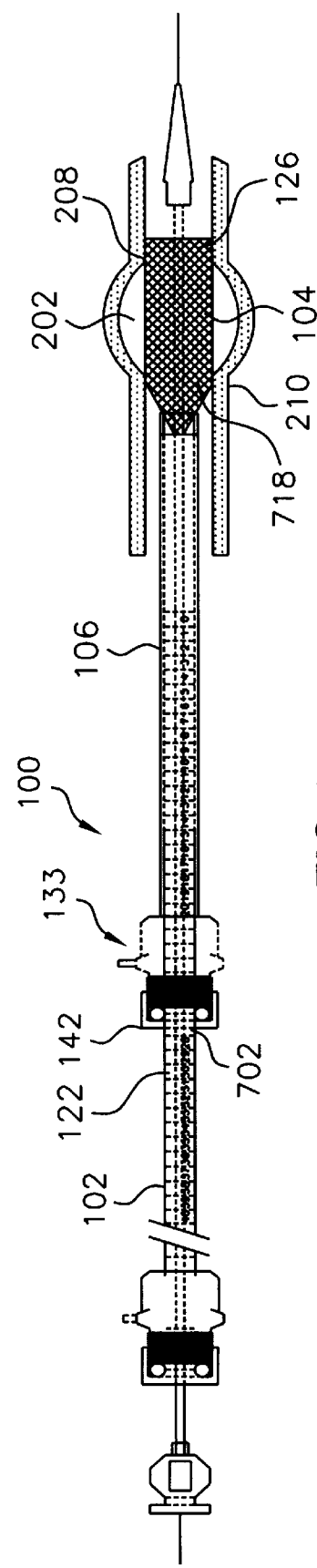

METHOD OF MEASURING A BODY CAVITY

This application is a division of U.S. patent application Ser. No. 08/466,934 filed Jun. 6, 1995 now abandoned.

BACKGROUND OF THE INVENTION

1. Field of the Invention

This invention relates broadly to a measuring and testing apparatus for measuring the size of a stent in a body vessel and for determining the effect of the stent on surrounding tissue and organs. More particularly, this invention relates to an apparatus and a method for measuring the length of a tubular braided stent needed for use in a blood vessel, and to stent loading and deployment apparatus and methods. The invention also relates to methods for determining whether a stent, when deployed, will block important connecting vessel, and whether such blockage would be detrimental to the patient.

2. State of the Art

Transluminal prostheses are well known in the medical arts for implantation in blood vessel, biliary ducts, or other similar organs or the living body. These prostheses are commonly known as stents and are used to maintain, open, or dilate tubular structures or to support tubular structures that are being anastomosed. When biocompatible material are used as a covering or lining for the stent, the prosthesis is called a stent-graft or endoluminal graft. If used specifically in blood vessels, the stent-graft is known as an endovascular graft. A stent may be introduced into the body by stretching it longitudinally or compressing it radially, until its diameter is reduced sufficiently so that it can be fed into a catheter. The stent is delivered through the catheter to the site of deployment and then released from the catheter, whereupon it self-expands. The contraction to stretching ratio and radial pressure of stents can usually be determined from basic braid equations. A thorough technical discussion of braid equations and the mechanical properties of stents is found in Jedweb, M. R. and Clerc, C. O., "A Study of the Geometrical and Mechanical Properties of a Self-Expanding Metallic Stent—Theory and Experiment", *Journal of Applied Biomaterials;* Vol. 4, pp. 77–85 (1993). In light of the above, it becomes evident that a stent must possess certain elastic and compression qualities.

A typical state of the art stent, such as disclosed in U.S. Pat. No. 4,655,771 to Wallsten or in U. K. Patent Number 1,205,743 to Didcott, is shown herein in prior art FIGS. 1, 1a, 2, and 2a. Didcott and Wallsten disclose a tubular body stent 10 composed of wire elements 12, each of which extends in a helical configuration with the centerline 14 of the stent 10 as a common axis. Half of the elements 12 are wound in one direction while the other half are wound in an opposite direction. With this configuration, the diameter of the stent is changeable by axial movement of the ends 9, 11 of the stent. Typically, the crossing elements form a braid-like configuration and are arranged so that the diameter of the stent 10 is normally expanded as shown in FIGS. 1 and 1a. The diameter may be contracted by pulling the ends 9, 11 of the stent 10 away from each other as shown by the arrows 16, 18 in FIG. 2. When the ends of the body are released, the diameter of the stent 10 self-expands and draws the ends 9, 11 of the stent closer to each other.

The fact that stents undergo various dimension changes from their compressed form to their uncompressed form, results in complications in placement. Placement of a stent having any degree of elongation and radial force as a result of compression is very difficult for several reasons. First, the stent, depending on its pitch angle, may have to be pushed out of the catheter over a long distance. This may be extremely difficult in light of the increased friction forces and various bent sections encountered in the catheter as it traverses a tortuous path. Second, the stent may conversely shrink significantly in length as its diameter expands, thereby rendering it difficult to accurately place it in a vessel. Third, plaque, thrombus or other protrusions or inclusions in the blood vessel lumen may alter the diameter of the stent which consequently alters the length of the stent. The importance of extreme accuracy in placement of an endovascular graft (EVG) will be appreciated by those knowledgeable in the art. For example, in aneurysmal vessel disease, such as that encountered in the abdominal aorta where the distance between the renal arteries and the aneurysm is quite short (less than 3 cm), misplacement of an EVG over the renal arteries or only in the aneurysm can prove fatal.

Proper placement of the stent becomes impossible where the stent is too long or too short for the body cavity in which it is being deployed. In order to be effective, the dimensions of a vessel must be known very accurately and the stent must be tailored to match the specifications of the vessel.

Several difficulties arise, however, when trying to determine the proper stent length needed for any particular cavity. One such problem, especially present with the self expanding stent design such as described by Wallsten and Didcott, is that it is often difficult to predict exactly to what length the stent should be cut in order to properly fit within a particular blood vessel. For example, when deploying an EVG in an aortic aneurysm, the distal end of the stent may reside in the aneurysmal area if the stent is cut too short in length, thereby not sealing the aneurysm and causing potential problems, such as rupturing of the aneurysm. On the other hand, if the EVG is cut too long, the distal end of the EVG can extend into one of the iliac arteries which will lead to clotting of the contralateral iliac artery. Also, if deployed in a vessel with multiple branching, and EVG which is too long may inadvertently cover an arterial branch, thereby occluding the branch and starving the organ which it is intended to nourish.

It is known to presently approximate the deployment length of an EVG stent by using various angiographical techniques (x-ray examinations of blood vessels or lymphatics following the injection of a radiopaque substance). In particular, this is done by injecting radiopaque dye into a vessel and photographing the dye with an X-ray machine as it moves through the vessel. A shortcoming of this method, however, is that angiography usually produces only two-dimensional views of the vessels being examined which are limited by the plane in which the x-ray is taken. As a result, angiograms often fail to reveal the presence of tortuous paths of the examined vessel which may be going in and out of the plane of the angiogram. In addition, the EVG may expand in the area of the aneurysm, depending on the fibrin (the insoluble protein end product of blood coagulation, formed from fibrinogen by the action of thrombin in the presence of calcium ions) content in the aneurysm, and contract in the narrow areas of the aneurysm, thus rendering any prediction of the necessary stent size difficult. It is also known to use Computerized Tomography (CT) scans and the like to show arterial diameters from which the desired deployment stent length can be extrapolated. The prediction of stent deployment length based solely upon slices of diameter, as well as the non-predictability of the fibrin content in an aneurysm, however, limit the accuracy of CT scans. Other more novel methods for visualizing vessels include spiral CT scan and intravascular ultrasound (IVUS).

Besides sharing some of the same disadvantages of angioscopy and CT scans, the spiral CT scan provides an image of the outside of the blood vessel only, and therefore fails to show the inside of the vessel where plaque and thrombus accumulate and where the stent is to be placed. The IVUS suffers from not visualizing the compressibility of fibrin and not providing a readout of vessel diameter and length. Another disadvantage shared by the aforementioned apparatus, is that they only provide instantaneous views of the vessel, and may therefore not be accurately representative of the vessel diameter during systole or diastole of the vessel.

Another problem encountered with stenting, especially with coated stenting (EVG deployment), is that branch arteries are often occluded. For example, when correcting an aortic aneurysm, an EVG is deployed between the neck of the proximal portion of the aneurysm below the renals to the bifurcation, or in the case of a bifurcated EVG, to the iliac arteries or beyond. As a result, the EVG may occlude arteries such as the lumbar arteries, intercostal arteries and even the mesenteric artery. In general, occlusion of these arteries is not detrimental to the patient as the mesentery and the spinal chord are fed by other collateral arteries. In a small number of patients, however, blockage of these arteries can result in paraplegia.

SUMMARY OF THE INVENTION

It is therefore an object of the invention to provide an apparatus and method for measuring the length of a stent or endovascular graft in a body vessel which provides accurate results.

It is also an object of the invention to provide an apparatus and method for measuring the length of a stent or endovascular graft in a body vessel which is easy to use.

It is another object of the invention to provide a method for temporarily blocking a branch of a body vessel and determining if this blockage is detrimental to the patient.

It is a further object of the invention to provide an apparatus and method for measuring the length of a stent or endovascular graft in a body vessel which includes a stent made from a resiliently deformable material.

It is another object of the invention to provide an apparatus and method for measuring the length of a stent or endovascular graft in a body vessel which includes a plunger and a sheath for introducing and placing a stent in a body vessel.

It is an additional object of the invention to provide an apparatus for temporarily blocking a branch vessel where the apparatus includes a stent made from a resiliently deformable material which is coated with another resiliently deformable material which is capable of blocking a branch vessel.

A further object of the invention is to provide an apparatus and method for measuring the length of a stent or endovascular graft in a body vessel which includes a calibrated scale.

Another object of the invention is to provide an apparatus and method for measuring the length of a stent or endovascular graft in a body vessel which includes a hollow catheter.

An additional object of the invention is to provide an apparatus and method for loading and deploying a length of stent or endovascular graft which was measured according to methods of the invention.

According to the invention, an apparatus for measuring the desired length of a prosthetic device which is to be implanted in a predetermined body cavity of a patient generally includes a helically coiled stent formed of a resiliently-deformable material with or without a coating, a plunger and sheath for inserting the stent into the body cavity and removably deploying the stent in the body cavity, and a measurement device for measuring an indication of the length of the stent once deployed in the body cavity. The apparatus may be constructed with a catheter having a lumen which accommodates a guide wire, thereby facilitating guiding the apparatus into the body cavity, and with a dilator tip to facilitate maneuvering of the catheter through the vasculature.

In the preferred embodiment of the invention, the proximal end of the stent is attached to the distal end of the plunger, the proximal end of the plunger is marked with a scale which is calibrated proportionally to the length of stent when in the compressed state, and the sheath is translatably adjustable over the plunger. Thus, movement of the sheath relative to the plunger deploys the stent from the sheath such that the stent is free to expand in the vessel in which it is being removably deployed. The amount of movement of the sheath relative to the plunger can be measured on the scale. The reading on the calibrated scale represents the "at rest" or fully uncompressed length of the stent being deployed by the sheath and plunger.

Other preferred aspects of the invention include a sheath to plunger lock or stop at the proximal end of the sheath which contains a threaded hub and a compressible O-ring, and a plunger to catheter lock at the proximal end of the plunger which also includes a threaded hub and a compressible O-ring. The threaded hub and compressible O-ring of the sheath to plunger lock are used to prevent unintentional motion of the sheath relative to the plunger, as well as serving as a hemostasis valve during an interventional surgical procedure. The threaded hub and compressible O-ring of the plunger to catheter lock serves as an additional hemostasis valve. If desired, a radiopaque medium can be dispensed at the distal end of the hollow catheter to permit the user to monitor the progress of the apparatus.

In further accord with the objects of the invention, a method of measuring the desired length of a prosthetic device which is to be implanted in a body cavity of a patient using the measuring apparatus of the invention is provided. According to the method of the invention, the helically coiled stent of the apparatus is placed and deployed within the body cavity via the placement means of the apparatus. Once sufficient length of the stent is deployed within the body cavity to span the desired length, the measuring device of the apparatus is used to determine the length to which the stent is to be cut. The apparatus is then removed from the body cavity, and the stent of the apparatus, or an equivalent stent, is cut to the measured length.

In the preferred method of the invention, a guide wire is first maneuvered through the body cavity where a stent is to be deployed until it reaches a point slightly beyond the deployment site. The sheath of the apparatus is then fully extended over the stent of the apparatus such that the stent is completely compressed within the sheath. The apparatus is then threaded along the guide wire via the hollow inner catheter of the apparatus until properly positioned within the body cavity. The user can monitor the progress of the compressed stent by use of a fluoroscope and radiopaque media which is carried and disseminated alongside the apparatus as it travels through the patient. In addition, the catheter and stent are themselves preferably radiopaque, thereby further aiding visualization under fluoroscopy. Once in position, the sheath of the apparatus is retracted while holding the plunger stationary. The portion of the compressed stent which is uncovered by the sheath deploys within the body cavity by expanding radially and decreasing in length. Retraction of the sheath continues until the user determines via fluoroscopy that the area of the body cavity to be bridged by the stent is fully bridged. At that point, i.e., once the appropriate length of stent has been deployed, the position of the stop of the sheath relative to the scale is read. Since the scale is calibrated, the values obtained will correspond directly to the length of the uncompressed stent which is required to bridge the body cavity. After the measurement has been taken, the sheath is re-extended over the stent, thus compressing it once again for easy removal from the body cavity. A separate stent is then prepared to the indicated length, and may be deployed in the body cavity by any known means in the art. Alternatively, the stent used to measure the cavity can be used by cutting it from the measuring device to the indicated length and placing it in the body cavity accordingly.

According to yet other aspects of the invention, a detachable hub is secured onto the proximal end of the inner catheter, and the plunger to catheter lock is made removable. Using this arrangement, the stent length measurement is conducted as summarized above. Once the measurement is read, the measuring device is entirely removed from the body, the proximal detachable hub is removed, the detachable plunger to inner catheter lock is removed, and the distal end of the catheter is pulled until the catheter is removed from the hollow plunger. The plunger connected to the stent is then pulled proximally until the stent is removed from the sheath. The stent is then marked from its distal end to the required length, and the proximal end of the plunger still connected to the stent is inserted into the sheath to plunger lock until the proximal end of the plunger sticks out of the distal end of the sheath. The proximal end of the plunger is pulled out of the distal end of the sheath until the stent is pulled through the sheath and out of the distal end of the sheath to the marking. The stent is then cut proximal of the marking such that the stent in the sheath is of the desired size, and the plunger containing the remaining end of the stent can be discarded; or alternatively the remaining portion of the stent can be severed from the plunger so that the plunger can be reused. With the stent loaded, the introducer system is preferably reassembled with the detachable hub, the detachable plunger to catheter lock, and a new or reused plunger.

Additional objects and advantages of the invention will become apparent to those skilled in the art upon reference to the detailed description taken in conjunction with the provided figures.

BRIEF DESCRIPTION OF THE DRAWINGS

FIG. 6 is a broken transparent side view of the endovascular measuring apparatus of the invention deploying the stent within a body cavity such that the stent partially bridges the body cavity;

FIG. 7 is a broken transparent side view of the endovascular measuring apparatus of the invention deploying the stent within a body cavity such that the stent fully bridges the body cavity;

DETAILED DESCRIPTION OF THE PREFERRED EMBODIMENT

The entire disclosure of U.S. patent application Ser. No. 08/466,934 filed Jun. 6, 1995 is expressly incorporated by reference herein.

Figure 1:
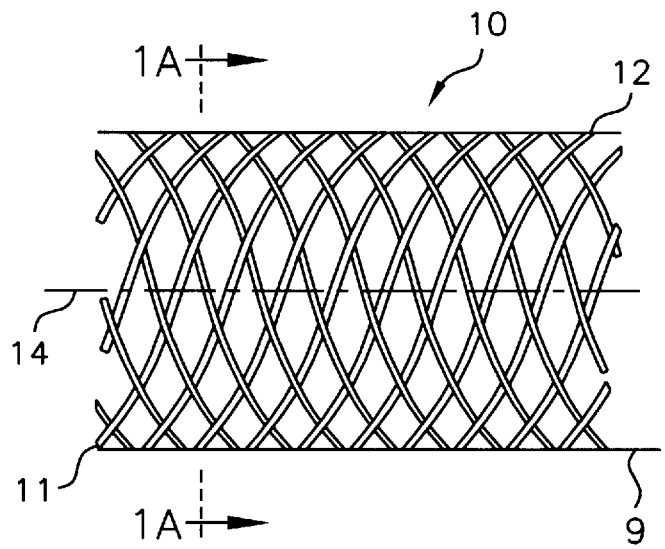
FIG. 1 is a broken side elevation view of a prior art stent expanded in a non-stressed position.
Figure 1A:
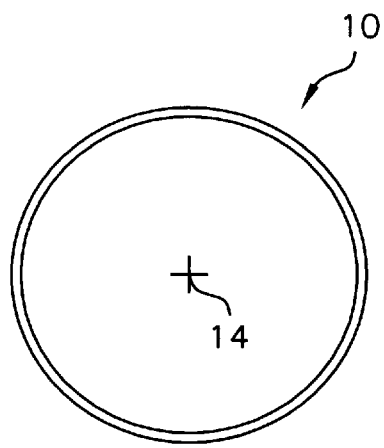
FIG. 1a is a cross sectional view along line 1A—1A of FIG. 1.
Figure 2:
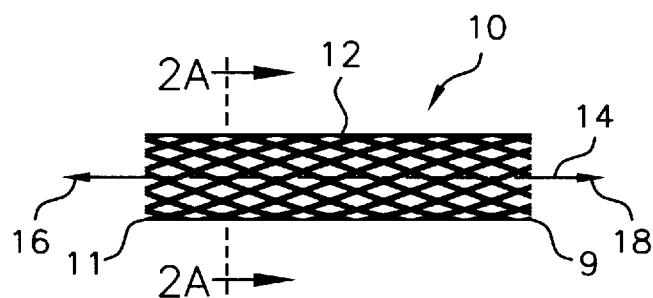
FIG. 2 is a broken side elevation view of a prior art stent stretched and contracted.
Figure 2A:
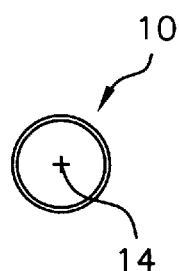
FIG. 2a is a cross sectional view along line 2A—2A of FIG. 2.
Figure 3:
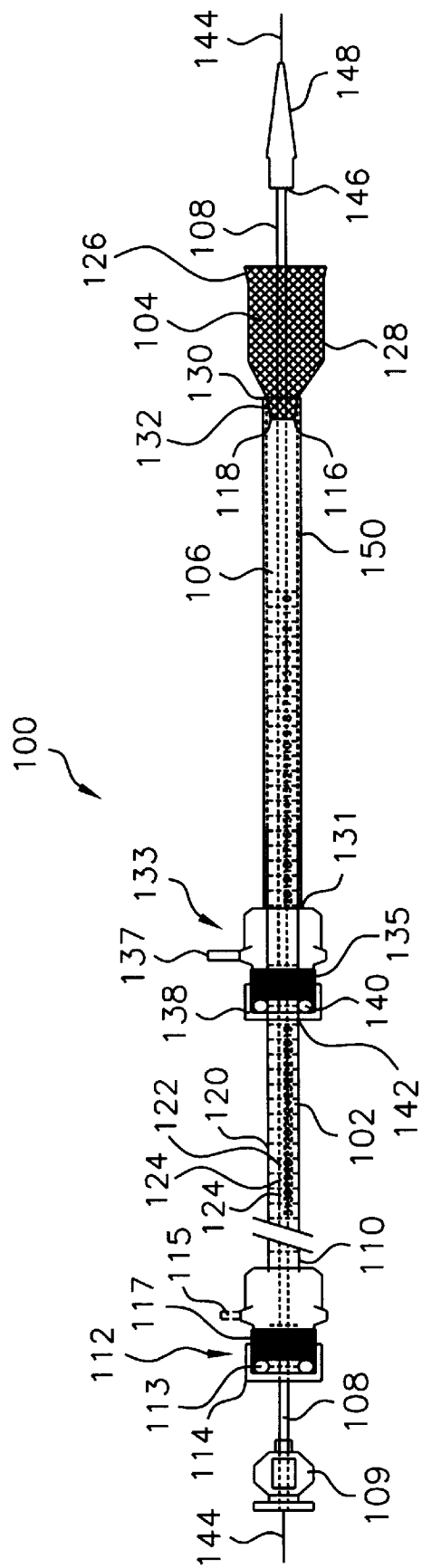
FIG. 3 is a broken transparent side view of the endovascular measuring apparatus of the invention with its sheath retracted.

Turning now to FIG. 3, the endovascular measuring apparatus 100 of the invention broadly includes a hollow plunger 102, a wire stent 104, a hollow sheath 106, and a hollow inner catheter 108 attached to a hub 109. The plunger 102 has a proximal end 110 with a first locking hemostasis valve 112 and a distal end 116 which is affixed to the proximal end 118 of the stent 104. The hemostasis valve 112 includes an O-ring 113, and a locking cap 114. The lumen (not shown) of the hollow plunger 102 is dimensioned such that it can slide freely over the body of the hollow inner catheter 108. The hollow inner catheter 108 serves as a guide for a guidewire 144 and as a tether to hold a soft flexible hollow dilator tip 148 in place at the distal end 146 of the catheter 108. The tip 148 can be adjusted relative to the distal end 116 of the plunger 102 by sliding the inner catheter 108 within the plunger 102.

Once the tip 148 is adjusted to accommodate the compressed stent 104, the inner catheter 108 is locked into place by tightening the cap 114 onto a threaded portion 117 of the first locking hemostasis valve 112. The cap 114 is effectively a locking mechanism which compresses the O-ring 113, thereby fixing or locking the plunger 102 relative to the inner catheter 108 and the tip 148. The body 120 of the plunger 102 contains a calibrated scale 122 having, e.g., fifty major divisions 124 spaced at calibrated intervals. The scale 122 is calibrated to adjust for the longitudinal length contraction and diameter expansion experienced by the particular stent 104 when being decompressed; i.e., the ratio of the length of the stent when in the sheath to the length of the stent when uncompressed.

The proximal end 118 of the wire stent 104 is affixed to the distal end 116 of the plunger 102 by any desirable means such as by heat fusing, insert molding, or gluing with epoxy. The body 128 of the wire stent 104 when uncompressed has a diameter larger than that of the plunger 102 and of the sheath 106.

The distal end 130 of the sheath 106 is open, and the sheath 106 has a diameter slightly larger than that of the body 122 of the plunger 102 so as to be translatable along the plunger body. The sheath 106 is further translatable over the stent 104 due to flexible and deformable characteristics of the stent 104. It will be appreciated that when the sheath 106 is positioned over the wire stent 104, the stent 104 contracts and elongates in a manner similar to that discussed in the Background of the invention and shown at 132.

The proximal end 131 of the sheath 106 is attached to a second hemostasis valve 133 which is preferably provided with external threads 135. A second threaded cap 138 containing a second compressible O-ring 140 is screwed onto the proximal end of a second locking hemostasis valve 133. The second threaded cap 138 mates with the threads 135 of the second locking valve 133 to reversibly fasten the sheath 106 to the plunger 102. The O-ring is used both to prevent inadvertent slippage of the sheath 106 relative to the plunger 102 by acting as a friction-locking mechanism, and to serve as a hemostasis valve during interventional surgical procedures. By pulling the first locking valve 112 away from the second locking valve 133 (or pushing the sheath 106 relative to the plunger 102), the wire stent 104 can be pulled into the sheath 106 and compressed. Conversely, by pushing the first locking valve 112 toward the second locking valve 133 (or pulling the sheath 106 relative to the plunger 102), the distal end 126 of the wire stent 104 can be released and will expand towards its relaxed uncompressed configuration until (and if) constrained by the blood vessel in which it is being deployed. It will be appreciated that the second locking valve 133 can be positioned and will lock anywhere along the body 120 of the plunger 102, thus providing the user with a means to control the length of stent 104 to be deployed. By reading the scale 122 at the location of the proximal-most end 142 of the second locking valve 133, the length of stent required for deployment within the body cavity 202 at any given time can be determined. In particular, since the scale 122 is preferably calibrated to the ratio of the length of the stent 104 when compressed in the sheath 106 to the length of the stent 104 in its uncompressed state, the reading provided on the calibrated scale will inform the practitioner as to the length of uncompressed stent required to bridge any cavity in any path, regardless of the state that the stent will assume when deployed in the cavity.

Figure 4:
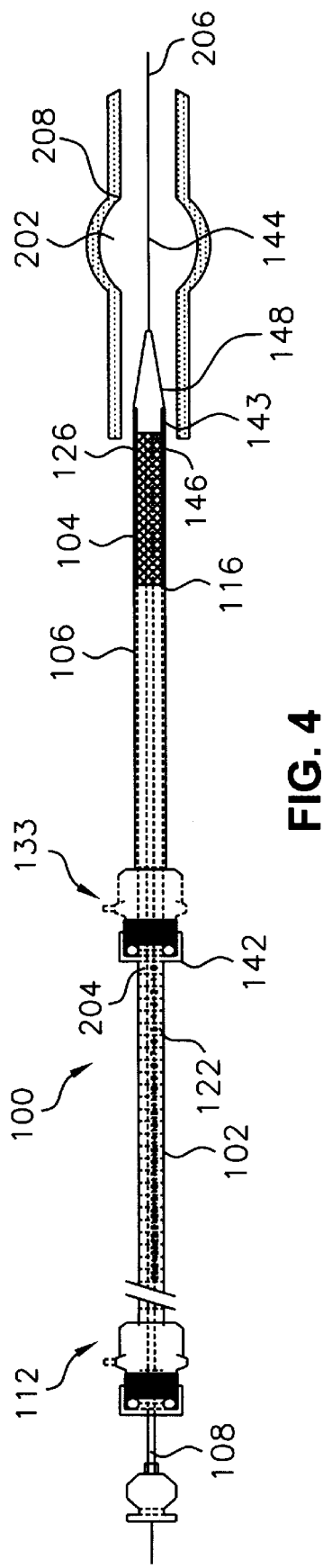
FIG. 4 is a broken transparent side view of the endovascular measuring apparatus of the invention when partially inserted within a body cavity and with its sheath fully extended.
Figure 5:
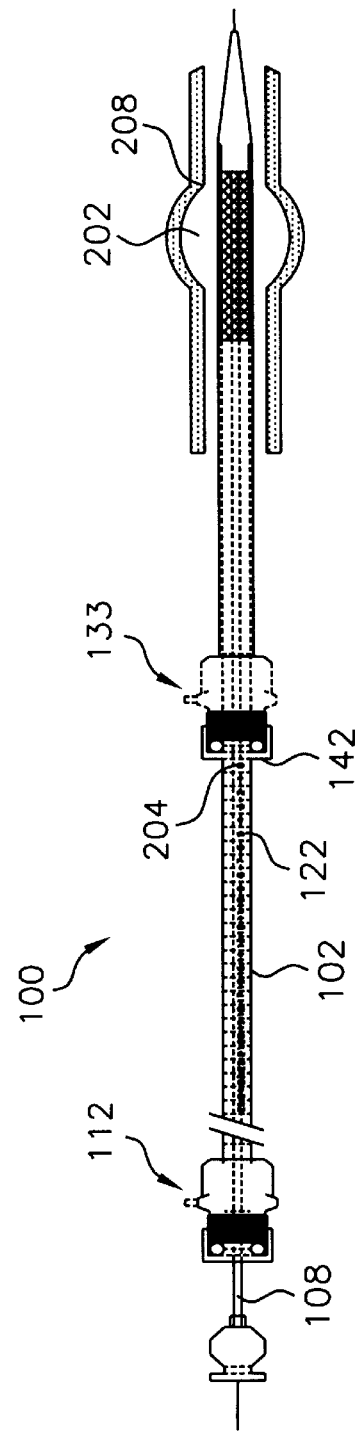
FIG. 5 is a broken transparent side view of the endovascular measuring apparatus of the invention when fully inserted within a body cavity and with its sheath fully extended.

Still referring to FIG. 3, it is noted that both the first and second locking hemostasis valves 112, 133 are preferably provided with flushing lines 115, 137. The lines 116 and 137 permit the spaces between the concentric hollow sheath 106, hollow catheter 108, and hollow plunger 102 to be flushed with heparinized saline during the insertion procedure. It is also seen that the hollow catheter 108 extends from the proximal hub 109 past the open distal end 126 of the stent 104. The catheter 108 has an interior lumen (not shown) dimensioned for following a guide wire 144 into the body cavity 202 (see FIG. 4) of a patient. The distal end 146 of the catheter 108 is coupled to the hollow dilator tip 148. The hollow catheter 108 and dilator tip 148 are capable of transporting a radiopaque contrast medium (not shown) used for fluoroscopic viewing.

The plunger 102 and the sheath 106 of the apparatus 100 can be made from any durable biocompatible material such as nylon, polyurethane, Teflon®, polyester, PVC, polyethylene, polypropylene, etc., or various combinations of the above, with or without radiopaque fillers such as barium sulfate or bismuth subcarbonate. The dilator tip 148 can be formed of the same materials as the plunger 102 and sheath 106, but is preferably formed of a softer durometer material such as Shore 80A polyurethane or Pebax nylon with a radiopaque filler or a radiopaque marking band. The measuring apparatus 100 of the invention can be made disposable or reusable. The lumen (not shown) of the inner catheter 108 or the annular space 150 between the sheath 106 and plunger 102 can be used to inject radiopaque contrast media into the vessel to assist in placement of the apparatus 100 as discussed above. The stent 104 material can be of the same material and of similar geometry as would be used in an EVG, or it may be of a more radiopaque material such as tungsten, stainless steel, gold and the like. The apparatus 100 can be used in virtually any cavitous area of the body such as the urethra, esophagus, biliary duct, blood vessels, etc. or in any surgically made duct or shunt such as those made in the liver during transjugular intrahepatic portosystemic shunt procedures.

Referring now to FIGS. 4–7, the apparatus 100 of the invention is seen with reference to the method of the invention. According to the method of the invention, the measuring apparatus 100 of the invention is initially placed in its fully axially extended position (see FIG. 4), with the sheath 106 covering the entire length of the wire stent 104 which is in turn fully compressed. In this configuration, the second locking valve 133 of the sheath 106 is at its furthest distance from the first locking valve 112 of the plunger 102, and is aligned with the scale 122 such that the proximal most end 142 of the stop coincides with the "0" mark 204 on the scale 122. The tip 148 is adjusted to fit into the sheath 106 by loosening the first locking valve 112 and pulling the inner hollow catheter 108 proximally such that the stepped proximal end 143 of the tip 148 fits into the sheath 106 and the distal end 116 of the plunger 102 abuts the proximal end 118 of the compressed stent 104. Tile distal end 206 of the guide wire 144 is located sufficiently past the body cavity 202 to allow proper placement of the measuring apparatus 100. When positioning the measuring apparatus 100, the distal ends of the stent 104 and sheath 106 should typically be located slightly past the distal neck 208 of the body cavity 202 in which the stent 100 is to be deployed (see FIG. 5). This is done to compensate for the tendency of the stent 104 to contract in length when going from its compressed configuration in the sheath 106 to its deployed configuration in the vessel 202. It should be noted that the flexible hollow dilator tip 148 at the distal end 146 of the catheter 108 is radiopaque. Thus, a user may monitor the progress and placement of the measuring apparatus 100 by means of a ti fluoroscope (not shown).

Once the measuring apparatus 100 is properly positioned within the body cavity 202 (as in FIG. 5), the sheath 106 is slowly retracted (see FIG. 6) by first loosening the cap 138 on the second locking valve 133 and then, while holding the plunger 102 stationary, pulling the sheath 106 backwards. As the sheath is retracted, the distal end 126 of the stent 104 is released and expands back towards its uncompressed configuration until it engages the distal neck 208 of the cavity 202. It will be appreciated that, as the distal end 126 of the stent 104 has an at rest uncompressed diameter greater than the distal neck 208 diameter of the body cavity 202, the distal end 126 of the stent exerts pressure on the distal neck 208 when it is deployed, causing the distal end 126 of the stent 104 to be locked into place. As mentioned above, the overall length of the stent 104 decreases when it goes from its compressed configuration to its less compressed deployed configuration. It is thus important that the user position the distal end 126 of the stent 104 sufficiently past the distal neck 208 of the body cavity 202 to compensate for this shrinkage. It will be noted, however, that should the practitioner discover after the sheath 106 has been retracted that the distal end 126 of the stent 104 is not positioned far enough into the distal neck 208 of the body cavity 202, the practitioner need only re-extend the sheath 106 fully over the stent 104 and repeat the above steps of positioning.

As indicated by FIG. 7, the sheath 106 is further retracted until the user determines, via fluoroscopy, that the stent 104 is sufficiently deployed so as to bridge the length of the body cavity 202. As shown in FIG. 7, the length of stent 104 as retractably deployed must be slightly longer than the length of the body cavity 202. In this manner, the proximal end 718 of the length of retractably deployed stent 104 and the distal end 126 of the stent are positioned respectively within the proximal and distal necks 210, 208 of the body cavity 202. Once the desired length of stent 104 is retractably deployed, the proximal most end 142 of the second locking valve 133 is used as an indicator on the scale 122 of the plunger 102. As discussed above, the scale 122 is calibrated such that the indicated number 702 represents the uncompressed length of stent needed to fully bridge the body cavity 202. In this particular case, the scale 122 indicates 27 mm, signifying that a stent having an at rest, uncompressed length of 27 mm must be used to properly bridge the body cavity 202 which may be, e.g., 20 mm long.

Once the measurement is taken, the sheath 106 is re-extended over the stent 104 (as in FIG. 5), thus re-compressing it, and the entire measuring apparatus 100 is withdrawn from the body cavity 202 and the patient. The stent 104 may then be detached from the measuring apparatus 100 by cutting it with, for example, scissors, or a new stent or covered stent (not shown) having the same properties and pitch angle as the stent 104 of the measuring apparatus 100, and having an at rest uncompressed length equal to or proportional to the recorded measurement, may be obtained. In the above example, a 27 mm stent of the same diameter and geometry would thus be obtained. This stent is then inserted into the body cavity 202 for deployment via any known means in the art. As the measurement method of the invention has already determined the proper stent length, the user is only left with the task of properly placing the stent within the body cavity 202.

Figure 8:
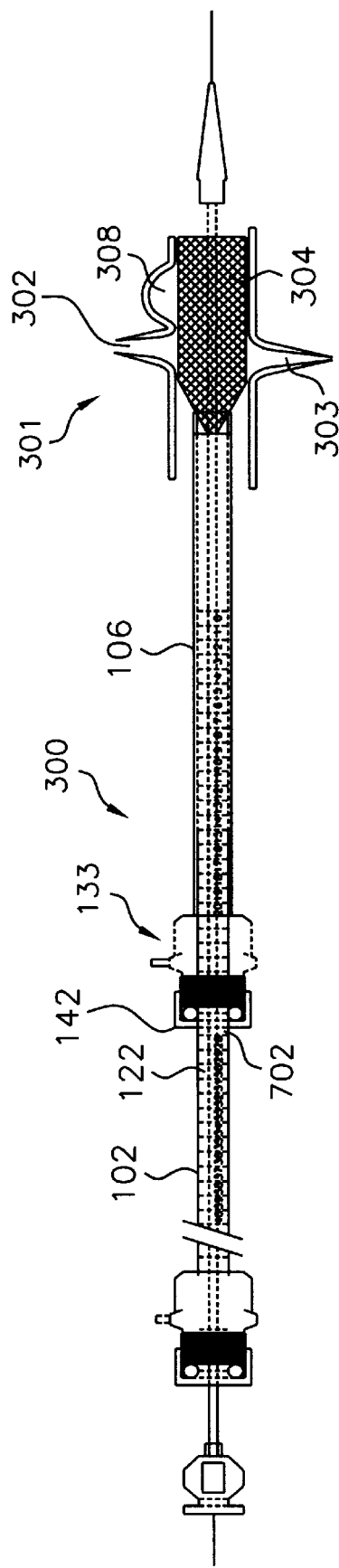
FIG. 8 is a view similar to FIG. 7 illustrating the measuring apparatus with a non-porous stent deployed in a body cavity having branching vessels.

Turning now to FIG. 8, a second embodiment of the apparatus 300 of the invention is seen. In this embodiment, the stent 304 of the measuring apparatus 300 is coated with a microporous or non-porous elastomeric membrane. The apparatus 300 has particular advantageous use where the body cavity 301 has several branching vessels 302, 303 and a saccular aneurysm 308. With the measuring apparatus 300 deployed inside the body cavity 301 as shown, the organs and tissues (not shown) fed by the branch vessels 302, 303 can be monitored to determine if they are suffering harmful effects as a result of the blocking of the branch vessels 302, 303 caused by the non porous stent 304. For example, if the branch vessels 302, 303 were to represent arteries which nourish the spinal chord, the lower extremities of the patient can be tested and monitored to determine if blocking of these arteries causes paraplegia in the patient. Should such a determination be made, the coated stent can either be cut shorter so as to not block the branch vessels, or the procedure terminated altogether. Similarly, when proceeding to bridge an aortic aneurysm, the measuring apparatus can be used with a coated stent to determine whether there is a back flow from, for example, a lumbar artery into the aneurysm, which if not occluded can lead to rupture of the aneurysm. If a back flow is detected, interventional blockage of the lumbar artery with an occlusion device may be required prior to stenting the aorta.

Figure 9:
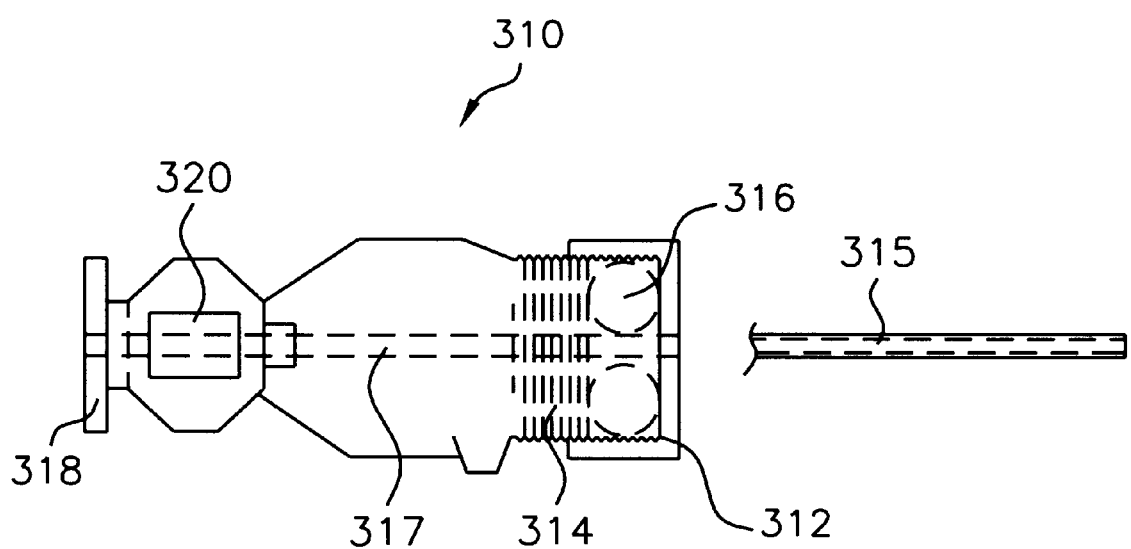
FIG. 9 is an enlarged view similar to FIG. 3 of a detachable proximal hub used in conjunction with a method of the invention for deploying the measured stent.
Figure 10:
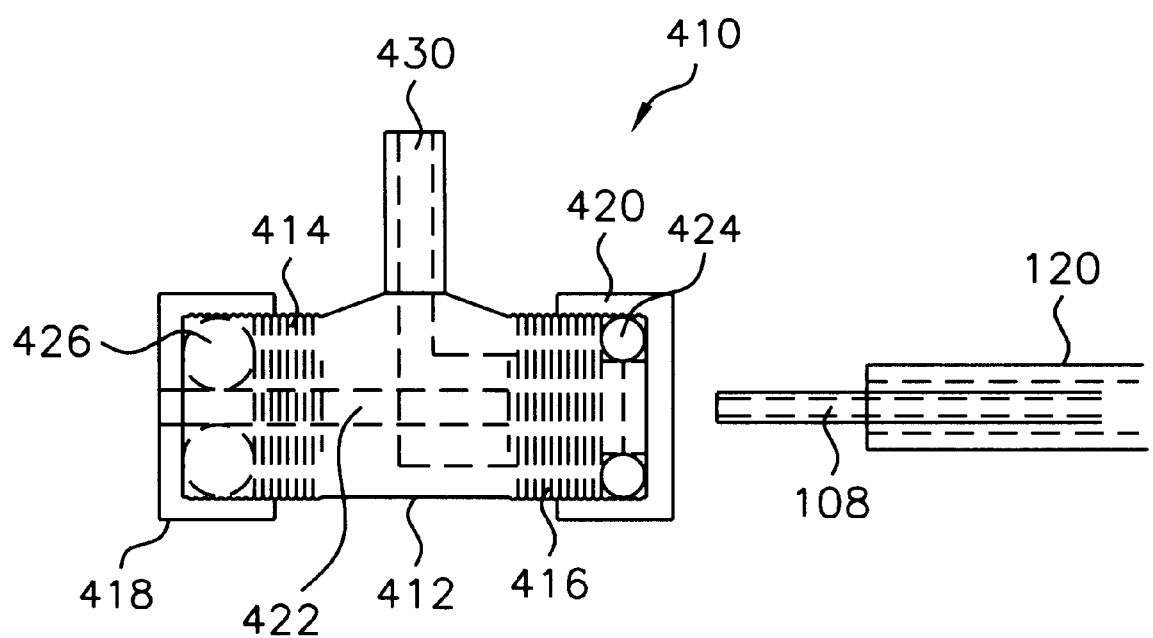
FIG. 10 is an enlarged view of similar to FIG. 3 of a detachable hemostasis valve used on conjunction with a method of the invention for deploying the measured stent.

In accord with yet another aspect of the invention, a detachable hub and detachable hemostasis valve for use in conjunction with methods for loading and deploying a stent or stent-graft are seen in FIGS. 9 and 10. In particular, a detachable hub 310 for use on the endovascular measuring apparatus 100 of FIGS. 3–8 (in lieu of hub 109) is seen in FIG. 9, having a cap 312 which screws onto threads 314, an O-ring 316, a lumen 317, and a proximal handle 318 having a luer lock 320 capable of connection to a hemostasis valve or the like. The inner catheter 315 is fed through the lumen 317 of the detachable hub 310 and locked into place by tightening the cap 312 onto the threads 314, thereby compressing the O-ring 316. Similarly, the detachable hemostasis valve 410 of FIG. 10 is intended to replace the valve lock 112 of FIGS. 3–8. The detachable hemostasis valve 410 includes a body portion 412 having proximal threads 414 and distal threads 416, distal and proximal caps 418, 420, a lumen 422, distal and proximal O-rings 424, 426, and a flush port 430. The inner catheter 108 and plunger 120 pass through the lumen 422, and when in place, the distal cap 420 can be tightened on the distal threads 416 to compress the distal O-ring 424 and lock the valve onto the plunger 120. Similarly, the proximal cap 418 can be tightened on the proximal threads 414 to compress the proximal O-ring 426 to lock onto the inner catheter 108. The flush port 430 can be used to enable flushing of the annular space between the plunger 120 and the inner catheter 108 with, e.g., heparinized saline.

With the detachable hub 310 and lock 410 as provided in FIGS. 9 and 10, the method of measuring a desired stent length can be carried out as described above with reference to FIGS. 3–8. However, in accord with another aspect of the invention, after the measurement, the provided apparatus can be used for loading and deployment of the measured stent or stent-graft. In particular, after the desired stent length has been measured, the entire measuring apparatus is removed from the body of the patient. Preferably, all lumens of the apparatus are then flushed with heparinized saline. The detachable hub 310 (FIG. 9) is then detached an removed, and the detachable lock 410 is detached and removed. With the hub 310 and lock 410 removed, the dilator tip 148 is grabbed an pulled distally, such that the inner catheter 108 is removed completely from the hollow plunger 120. Then, the stent 104 is pulled through and entirely out of the sheath 106. Using a waterproof, sterile, felt-tipped pen or the like, or any other desired mechanism, the stent of stent-graft 104 is marked to the desired length from its distal end 126 (e,g., 27 mm from the distal end of the stent). With the stent marked, the proximal end of the plunger 102, still connected to the stent 104, is inserted into the sheath, and through the plunger lock 133 until the proximal end 120 of the plunger sticks out of the distal end of the sheath 106; i.e., the plunger is inserted backwards through the sheath. The proximal end of the plunger sticking out to the distal end of the sheath is then pulled such that the stent or stent-graft 104 is pulled into the sheath and out of the distal end of the sheath to the mark. The stent 104 is then cut at, or just proximal to the marking such that the remaining stent (with the marking) with the plunger can be discarded, and the stent in the sheath properly loaded. With the sheath loaded, the introducer system is reassembled by inserting the catheter 108 through the sheath and stent, if desired, by providing a plunger to push out the stent or stent-graft 104 when properly located, and, if desired, by reattaching the hub 310 to the catheter, and the lock 410 to the plunger and catheter. It will be appreciated that the plunger utilized with the loaded sheath can be a new plunger used for deploying the stent 104, or the remaining portion of the stent utilized in the initial measurements with the excess stent removed from the plunger.

The loading and deployment method of the invention as set forth above have numerous advantages. It will be appreciated that since the stent is loaded by pulling the stent with the plunger, there is less opportunity for the stent wires to scrape and perforate the wall of the sheath. In addition, funnels usually required to load the stent are eliminate, and the stent loading operation is simple. Further, the stent or stent-graft being utilized is the same unit which was used as the measuring devise, thereby rendering the system less expensive.

There have been described and illustrated herein several embodiments of a tubular braided stent and a method of manufacturing the stent of the invention. While particular embodiments of the invention have been described, it is not intended that the invention be limited thereto, as it is intended that the invention be as broad in scope as the art will allow and that the specification be read likewise. Thus, while particular stent designs have been disclosed for use with the apparatus of the invention, it will be appreciated that other designs may work as well. For example, while a stent having a homogeneous pitch angle throughout has been disclosed, a stent with a different body and end pitch angle can also be used as disclosed in copending U.S. patent application Ser. No. 08/388,612, or continuously varying hyperbaloidal stents can be used. Furthermore while a particular mechanism for adjusting and locking the sheath relative to the plunger and a similar method for locking the plunger relative to the inner catheter has been disclosed, it will be understood that other mechanisms or no mechanisms may be used as well. Also, while a particular type of scale has been disclosed, it will be recognized that any other suitable scales could be used. For example, although a metric scale has been disclosed, an English system scale or any other measurement system scale could also be used. In addition, although a scale has been disclosed printed along the plunger body, the scale may instead include electronic measuring means coupled to an LCD readout. Furthermore, although the scale has been disclosed as having a particular calibration, any other calibration could be used. For example, although the scale has been calibrated to account for the contraction experienced by the stent when in an uncompressed configuration, the scale may be calibrated in any other fashion or may be uncalibrated. When uncalibrated, the practitioner can either conduct the necessary mathematics in order to determine the length of uncompressed stent to use, or can cut a stent in its compressed state in a sheath the same diameter as the sheath of the apparatus. In fact, if desired, no scale or calibration is necessarily required on the plunger, as the plunger can be marked by the practitioner during use, and measured afterwards. Although this measuring apparatus has been described for use with a self-expanding stent of the Wallsten or Didcott configuration, it will be appreciated that the measuring apparatus can be calibrated for use with other devices such as balloon expandable Palmaz or Gianturco stents and the like. The apparatus may also be used to acquire exact measurements of body cavities for data collection and subsequent use for other procedures such as bypass surgery, electrophysical mapping, endoscopic surgery, etc. Moreover, while a particular configuration for the dilator tip has been disclosed, it will be appreciated that other configurations or no dilator tip could be used as well. Furthermore, while a particular monitoring means has been described for use with the apparatus, it will be understood that any monitoring means can be similarly used. In particular, while the monitoring means were described to be fluoroscopy, other means such as radioscopy and CT scans may also be used. In addition, while a particular method of measuring the deployment length of a stent in a body cavity using the apparatus of the invention has been disclosed, it will be understood by those skilled in the art that details may be altered without changing the nature of the method. It will therefore be appreciated by those skilled in the art that yet other modifications could be made to the provided apparatus and method of the invention without deviating from their spirit and scope as so claimed.

What is claimed is:

1. A method of measuring the desired length of a prosthetic device which is to be implanted in a body cavity of a patient using a measuring apparatus having a stent formed of a resiliently-deformable material, a placement means for inserting and removably deploying said stent into the body cavity, and a measuring means for obtaining an indication of a length of said stent which was deployed in the body, said method comprising:

a) compressing the stent of the apparatus such that the diameter of the stent is less than the diameter of the body cavity;

b) locating the compressed stent within the body cavity;

c) using the placement means to removably deploy at least a first portion of the stent into the body cavity such that at least a portion of said first portion expands in diameter;

d) obtaining an indication of a length of the stent which was deployed in the body cavity; and e) removing the stent and the apparatus from the body cavity.

2. A method according to claim 1, wherein:

the stent is helically coiled.

3. A method according to claim 2, further comprising:

after obtaining an indication of a length of the stent which was deployed in the body and before removing the stent and the apparatus from the body cavity, capturing the entire stent with the placement means.

4. A method according to claim 2, further comprising:

f) cutting the stent to a length based on said indication obtained to obtain a cut stent.

5. A method according to claim 4, further comprising:

g) introducing the cut stent into the body cavity.

6. A method according to claim 4, wherein:

the measuring means of the apparatus is a calibrated scale, said obtaining an indication comprises viewing the calibrated scale, and said cutting to a length is to the length indicated by the calibrated scale.

7. A method according to claim 2, further comprising:

f) obtaining a stent of substantially identical characteristics to the stent which was removably deployed in the body cavity, the stent of substantially identical characteristics being of a length related to said indication obtained.

8. A method according to claim 7, further comprising:

g) introducing said stent of substantially identical characteristics into the body cavity.

9. A method according to claim 7, wherein:

the measuring means of the apparatus is a calibrated scale, said obtaining an indication comprises viewing the calibrated scale, and said obtaining a stent of substantially identical characteristics comprises obtaining a stent of a length indicated by the calibrated scale.

10. A method according to claim 2, wherein the placement means includes a sheath and a plunger, with a distal end of the plunger attached to the stent, and the plunger and stent being located in the sheath, said method further comprising:

f) removing the plunger and the stent from the sheath;

g) inserting the plunger proximal end first into proximal end of the sheath until the plunger and a desired portion of the stent extend out of a distal end of the sheath; and h) cutting the stent to a length based on said indication obtained, to obtain a cut stent loaded in the sheath.

11. A method according to claim 10, further comprising:

i) inserting said sheath with said cut stent into the body cavity; and j) pushing said cut stent out of said sheath so as to introduce said cut stent into the body cavity.

12. A method according to claim 1, wherein:

the stent has a coating which is either microporous or substantially non-porous, and the body cavity has one or more side vessels extending therefrom.

13. A method according to claim 3, further comprising:

f) after using the placement means to removably deploy at least a first portion of the stent into the body cavity such that at least a portion of said first portion expands in diameter, monitoring the patient to determine how the occlusion of the one or more side vessels of the body cavity by the stent affects the patient.

* * * * *